(12) United States Patent  (10) Patent No.: US 7,390,331 B2
Santin et al.  (45) Date of Patent: Jun. 24, 2008

(54) NASAL INSERTS (75) Inventors: Ernest Santin, Beverly, MA (US);
Louise MacDonald, Beverly, MA (US)

(73) Assignee: Sanostec Corp, Beverly Farms, MA (US)

( * ) Notice: Subject to any disclaimer, the term of this patent is extended or adjusted under 35 U.S.C. 154(b) by 0 days.

(21) Appl. No.: 10/434,669

(22) Filed: May 9, 2003

(65) Prior Publication Data

US 2003/0195552 A1  Oct. 16, 2003

Related U.S. Application Data

(63) Continuation-in-part of application No. 09/862,966, filed on May 22, 2001, now Pat. No. 6,562,057.

(51) Int. Cl.
*A61M 29/00* (2006.01)

(52) U.S. Cl. ............... 606/199; 128/204.12; 604/93.01; 604/94.01

(58) Field of Classification Search ............... 606/191, 606/196, 198, 199, 204.45; 128/200.24, 128/200.26, 206, 848, 858; 604/94.01
See application file for complete search history.

(56) References Cited

U.S. PATENT DOCUMENTS

| | | | |
|---|---|---|---|
| 682,123 | A | 9/1901 | Wilson |
| 753,133 | A | 2/1904 | Gamble |
| 810,617 | A | 1/1906 | Carence |
| 878,223 | A | 2/1908 | Meisselbach |
| 888,869 | A | 5/1908 | Clark |
| 1,034,123 | A | 7/1912 | Knowlson |
| 1,077,574 | A | 11/1913 | Woodward |
| 1,139,357 | A | 5/1915 | Garske |
| 1,160,797 | A | 11/1915 | Wallin |
| 1,256,188 | A | 2/1918 | Wilson |
| 1,311,461 | A | 7/1919 | Reynard |
| 1,322,375 | A | 11/1919 | Un |
| 1,481,581 | A | 1/1924 | Woodward |
| 2,010,485 | A | 8/1935 | Heath |
| 2,151,227 | A | 3/1939 | Pawelek |
| 2,264,153 | A | 11/1941 | Rowe |
| 2,277,390 | A | 3/1942 | Crespo |
| 2,335,936 | A | 12/1943 | Hanlon |
| 2,433,565 | A | 12/1947 | Korman |
| 2,515,756 | A | 7/1950 | Bove |

(Continued)

*Primary Examiner*—Michael J. Hayes
*Assistant Examiner*—Victor Nguyen
(74) *Attorney, Agent, or Firm*—Scott E. Kamholz; Foley Hoag LLP (57) ABSTRACT

A nasal breathing assist device includes a pair of open-ended tubular elements each extending along a central tube axis between a relatively large first end and a relatively small second end, a coupler element extending between the first ends of the tubular elements, and at least one non-resilient tab extends from the first end toward the second end of the tubular element. The tab includes at least one relatively small protrusion extending from a distal end of the tab toward the tubular element. The device may further includes a filer having a peripheral frame contoured to be snap-fitted in an open-faced channel defined within the tubular element. The device may further includes a removable medication carrier which is adapted to bear a therapeutic agent and adapted to insert into the open-faced channel of the tubular element. The tubular element may define at least one channels on an inner surface of the tubular element to receive edges of the medication carrier.

46 Claims, 11 Drawing Sheets

U.S. PATENT DOCUMENTS

| | | | |
|---|---|---|---|
| 2,569,743 A | 10/1951 | Carlock | |
| 2,663,297 A | 12/1953 | Turnberg | |
| 2,672,138 A * | 3/1954 | Carlock | 128/207.18 |
| 3,424,152 A | 1/1969 | Kuhlman | |
| 3,463,149 A | 8/1969 | Albu | |
| 3,710,799 A | 1/1973 | Caballero | |
| 3,742,943 A * | 7/1973 | Malmin | 606/204.45 |
| 3,802,426 A | 4/1974 | Sakamoto | |
| 4,105,035 A | 8/1978 | Rella | |
| 4,120,299 A | 10/1978 | Russo | |
| 4,414,977 A | 11/1983 | Rezakhany | |
| 4,573,461 A | 3/1986 | Lake | |
| 5,417,205 A * | 5/1995 | Wang | 128/206.11 |
| 5,425,359 A | 6/1995 | Liou | |
| 5,665,104 A * | 9/1997 | Lee | 606/199 |
| 5,775,335 A * | 7/1998 | Seal | 128/848 |
| 5,895,409 A | 4/1999 | Mehdizadeh | |
| 6,004,342 A | 12/1999 | Filis | |
| 6,561,188 B1 * | 5/2003 | Ellis | 128/206.11 |
| 6,562,057 B2 * | 5/2003 | Santin | 606/199 |
| 6,863,066 B2 | 3/2005 | Ogle | |

* cited by examiner

NASAL INSERTS

CROSS-REFERENCE TO RELATED APPLICATIONS

This application is a continuation in part of U.S. patent application Ser. No. 09/862,966, filed on May 22, 2001 now U.S. Pat. No. 6,562,057, the disclosure of which is incorporated herein by reference.

FIELD OF THE INVENTION

This invention pertains to methods and devices for nasal breathing assist devices, in particular to methods and devices for improving nasal breathing and reducing snoring.

BACKGROUND OF THE INVENTION

Snoring is a condition characterized by rough, loud, rattling breathing or inspiratory noise during sleep or deep coma. The characteristic snoring noise is produced by vibration of the soft palate (the soft tissue in the roof of the mouth near the throat) or vocal chords by inhaled or exhaled air. As the soft palate vibrates, the lips, cheeks, and nostrils may also vibrate, making the snoring louder.

Snoring can be caused by underlying physical or disease conditions that restrict air passages and force the patient to breathe with exaggerated force to move air through narrowed nasal passages. Chronic snoring can be the result of obstruction of larynx, upper airways, a deviated nasal septum, and blockages to the nose and nasal passages. Temporary snoring, or a sudden onset of snoring can be the result of stuffy and swollen mucus membranes, as with a cold or hay fever, or a nasal polyp.

Anatomical deformities in the airway such as large tonsils and adenoids, excessive length of the soft palate, or broken or crooked nose, can also diminish the airway size. Fat deposits around the upper airway, as found in obesity, can make the airway smaller. Low muscle tone in the muscles of the tongue and throat, or medications and foods (such as alcohol) that relax these muscles also increase snoring.

Snoring can causes relationship problems between partners, leading to a loss of intimacy and deterioration of relationships. Decreased sleep, or insufficient restful sleep increases irritability, poor memory and concentration and decreased work performance.

A number of methods and devices have been developed to reduce or eliminate snoring. Some devices are external to the patient and can include, buzzer systems and alarms that wake the patient. Special pillows, neck collars, chin braces and head straps have also been tested in an effort to control snoring. When snoring is caused by serious deformity, surgery has been performed to remove anatomical obstructions, such as removing tonsils, or correcting a deviated septum. Occasionally a procedure called UPPP (Uvulopalatopharyngoplasty) is recommended. This procedure acts like an internal facelift, tightening loose tissue. However, the success rate is only 50%. Laser surgery to correct airway defects is also available in some cases.

Other remedies include herbal potions and medications such as decongestants and anti-histamines. Diet and lifestyle changes may also reduce snoring to some degree.

Various devices have been developed that keep the mouth open, the tongue depressed, or nasal passages open. These dental devices can be expensive custom-fit, or inexpensive over the counter mouth pieces. Adhesive nasal strips, which are applied externally to either side of the nose, have been developed. While these strips may dilate the nasal passages to small degree, they do not work well in patients with anatomical deformities or obstructions in the nose. Air masks that force pressurized air into the mouth and lungs are available. These devices can be cumbersome, unsightly, painful, or expensive, and the patient may abandon these approaches in short time.

Sinusitis is another common nasal disease. Sinusitis is inflammation or infection of the mucous membranes that line the inside of the nose and sinuses. It can be caused by bacteria, viruses, and possibly by allergies. Chronic sinusitis is a prolonged sinus infection which generally last longer than 12 weeks. Chronic sinusitis is difficult to treat because it responds slowly to medications. Conventional treatment for chronic sinusitis includes oral antibiotics, nasal spray, and sinus surgery. These treatments generally cannot get directly to the source of the problem, or may cause side effect, for example, frequently using nasal spray may worsen the symptom.

SUMMARY OF THE INVENTION

The object of the present invention is to reduce snoring by increasing the airflow through the nasal passages. It is a further object to provide devices that improve nasal breathing by increasing airflow through the nasal passages during sleep. It is another object of the present invention to treat chronic sinusitis.

One aspect of the invention provides "dual tube" nasal breathing assist devices having a pair of open-ended tubular elements connected together by a coupler element. The tubular elements are preferably conic-frustum shaped along a tube axis, having a relatively large first end and a relatively small second end, and tapering from the first end to the second end along the tube axis. In some embodiments, each tubular element may have passageways extending through the tubular elements transverse to the tube axis. These passageways may be elongated, and extend at least in part in the direction of the tube axes.

The coupler element maintains the tubular element in a generally parallel relationship to each other in a common plane and in a spaced-apart relation which corresponds generally to the separation between the user's nostrils.

In one embodiment, the coupler element is a resilient, nominally curved strut lying in a plane substantially perpendicular to the tube axes, permitting relative angular motion of the tube elements about an axis perpendicular to the tube axes.

In an alternate embodiment, the coupler element is a resilient, nominally curved strut lying in a plane substantially parallel to the tube axes, permitting relative angular motion of the tube element about an axis parallel to the tube axes.

In another embodiment of the invention, a "single tube" nasal breathing assist device is a single, open-ended, resilient tubular element, adapted for insertion into a user's nostril. The tubular element is conic-frustum shaped, having a relatively large diameter first end and a relatively small diameter second end, and a taper extending from the first end to the second end along a tube axis. The tubular element may have passageways extending through the tubular element transverse to the tube axis. In one form, these passageways may be elongated. The single tube may be used in a user's nostril, and if desired, together with another single tube in the user's other nostril. In this form, the tubes are not coupled to each other.

In some forms of both the single tube or dual tube embodiments of the invention, the tubular elements have a tab extending from the first (i.e. relatively large) end which extends substantially parallel to the tube axis and is elongated in the direction of the tube axis. In yet another embodiment, each tube element has a tab support extending radially from the first end in a direction substantially perpendicular to the tube axis. At least one tab extends from the tab support, and is elongated in the direction of the tube axis. The tabs may be resiliently deformable, so as to permit elastic deformation in use, providing a frictional holding force when engaging the nose. Alternatively, the tabs may be non-resiliently deformable, permitting inelastic deformation, so that a user can "pinch" the tabs so that they capture and hold the nose. The non-resilient tabs are preferably made of metal, for example, copper, aluminum, but may be made of other materials that may be non-resiliently deformed. The tab preferably includes at least one relatively small protrusion extending from a distal end of the tab. The distal end is distal from the first end of the tubular element. The relatively small protrusion may also extend from the outer surface of the tubular element opposing the distal end of the tab. The tab and the protrusion help to prevent the device from slipping out of a user's nose.

The tubular element includes, preferably at its large end, an open-faced channel extending about its tube axis. The device further includes a filter having a peripheral frame contoured to snap-fit in the open-faced channel. The filter includes a filter medium, preferably a paper filter or metal or plastic mesh coated with absorbent materials, spanning the peripheral frame. In an alternate embodiment, at least one relative small protrusion extends from an inner surface of the channel. The filter is adapted to snap-fit over the protrusion into the channel and is retained by the protrusion, so that the filter cannot slip out from the channel when the device is in use. In a preferred embodiment, the protrusion extends throughout an inner circumference of the channel.

In another preferred embodiment, the device further includes at least one removable carrier which may include a medium, for example a metal or plastic mesh, or a surface, adapted to bear a therapeutic agent. The removable carrier preferably is a thin plate including two opposite edges. The tubular element further defines two opposing channels on an inner surface of the tubular element. The two opposing channels extend in a plane substantially parallel to the central axis and are adapted to receive the two opposite edges of said removable carrier. The therapeutic agent may be medications, for example, antibiotics, for treating chronic sinusitis or other nasal diseases.

Related objects and advantages of the present invention will be apparent from the following description.

BRIEF DESCRIPTION OF THE DRAWINGS

The foregoing and other objects of this invention, the various features thereof, as well as the invention itself, may be more fully understood from the following description, when read together with the accompanying drawings, in which.

DESCRIPTION OF THE PREFERRED EMBODIMENTS

The nasal breathing assist devices according to the various aspects of the invention are shown in FIGS. 1 through 10. These devices overcome the deficiencies in the currently available devices. The illustrated devices are small, inconspicuous in use, and require no special attachments or fittings. The devices are worn inside the nose, so that the nasal passages are kept open from the inside, rather than by external means. This allows the devices to maintain airways in noses where anatomical abnormalities diminish the effectiveness of externally applied strips. The devices can be used alone, or in conjunction with other snore-reducing aids, such as pillows and medicated nasal sprays.

Figure 1:
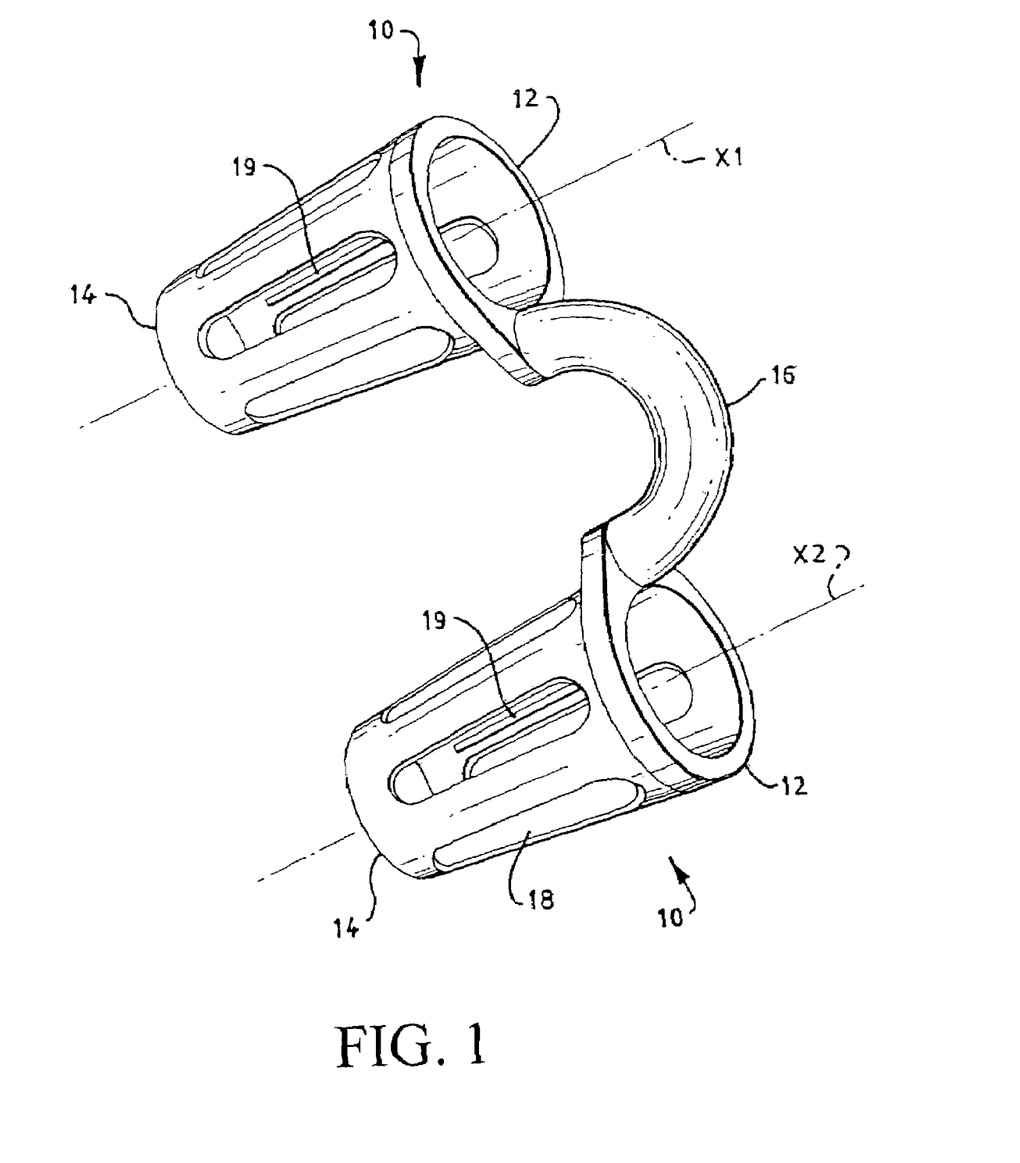
FIG. 1 is a perspective view of one embodiment of the present invention.

In the embodiment shown in FIG. 1, the nasal breathing assist device 1 comprises generally a pair of open ended tubular elements 10 connected together by a coupler element 16.

The tubular elements 10 are generally circular in cross section and extend a distance along tube axes X1 and X2 from first ends 12 to second ends 14. Preferably the tubular elements taper linearly from a relatively large diameter cross section along the tube axes X1 and X2 to a relatively smaller diameter cross section from the first end 12 to second end 14. The taper may be other than linear, for example, contoured to correspond generally to the taper inside the user's nostrils. First ends 12 also connect to the coupler element 16. In the illustrated form, the tubular elements 10 are conic-frustums, but other shapes may be used. For example, instead of circular cross sections, the tubular elements could have elliptical or other shaped cross sections. Further, instead of the inner diameter tapering monotonically from the large end to the small end, it could decrease initially, become larger, then decrease again.

The tubular elements 10 may also include at least one passageway 18 extending through the walls of the tubular elements transverse to the tube axes X1 and X2. The passageways 18 may be circular, elliptical, or elongated at least in part in the direction of the tube axes. Alternately, the passageways can be elongated in a direction extending circumferentially around the tube axes.

The coupler element 16 is a resilient, nominally curved strut which maintains the tubular elements spaced apart, with axes X1 and X2 in a substantially parallel relationship, and in substantially a common plane. The coupler element may be made of resilient, semi-rigid, or rigid material.

Grooves 19 inside of tubular elements are an additional feature which may be used to receive medication (nasal cream) before inserting in nasal passage so as not to irritate the skin inside the nasal passage, this allows the medication to be effective without contacting the nasal passage.

Figure 2:
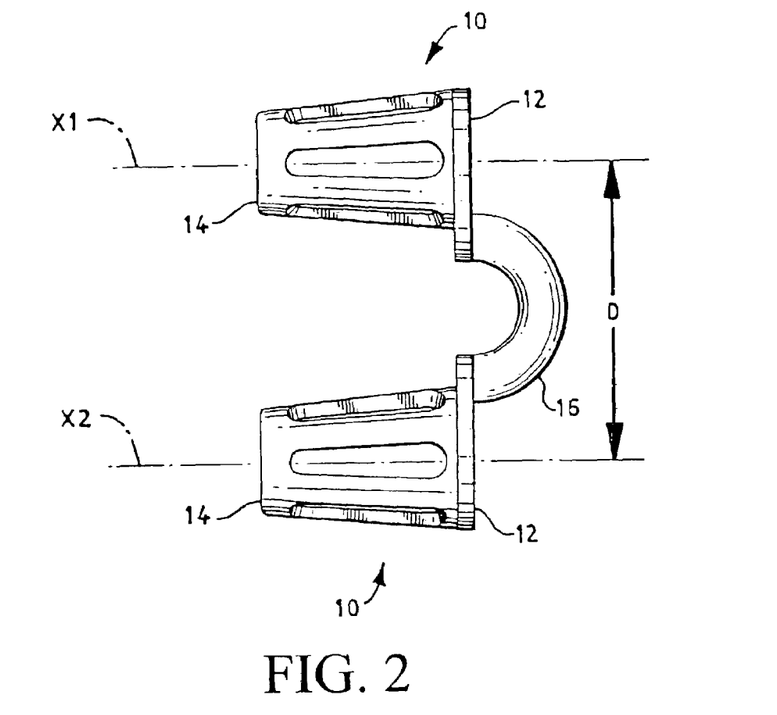
FIG. 2 shows a side view of the embodiment shown in FIG. 1.
Figure 3A:
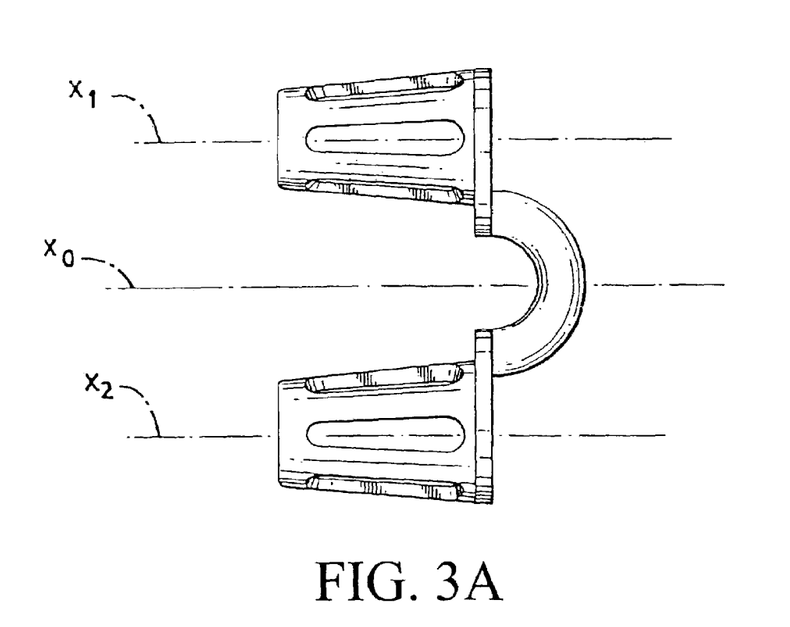
FIG. 3A shows a side view of an alternate embodiment of the invention.
Figure 3B:
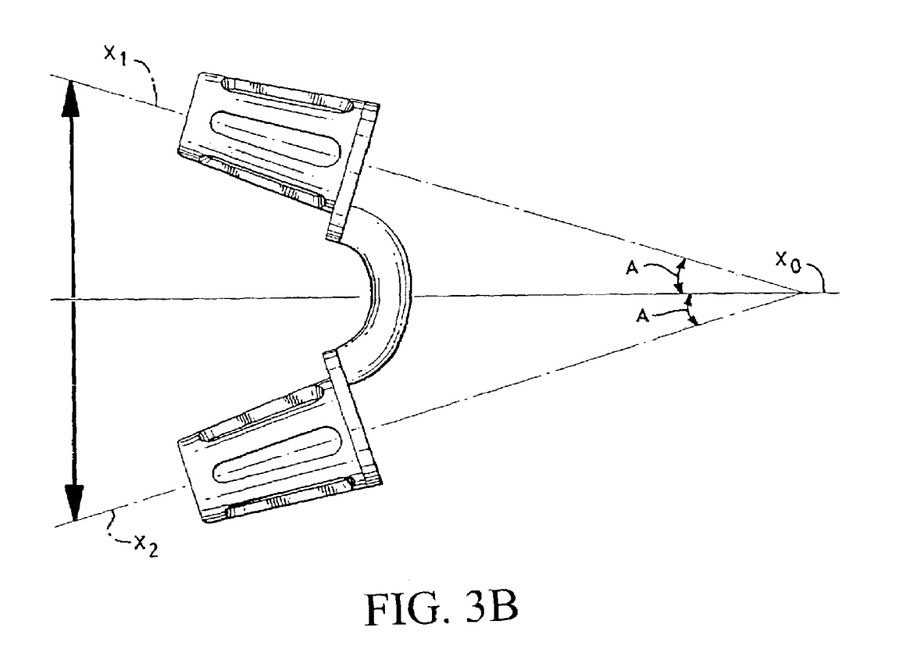
FIG. 3B shows a side view of the embodiment of FIG. 3A rotated about an axis.

As shown in FIG. 2, coupler element 16 maintains a nominal distance D between the tubular elements 10 that generally corresponds to the distance between the user's nostrils. In this embodiment, the coupler element extends in a plane that is essentially parallel to tube axes X1 and X2. As shown in FIGS. 3A and 3B, the resistance of coupler element 16 permits the axes X1 and X2 to be offset from an axis $X_0$ by angle A. Angle A can be as much as 15° or greater. Furthermore, in this embodiment, coupler element 16 permits relative flexing motion of the device about an axis, substantially perpendicular to the tube axes X1 and X2.

Figure 4A:
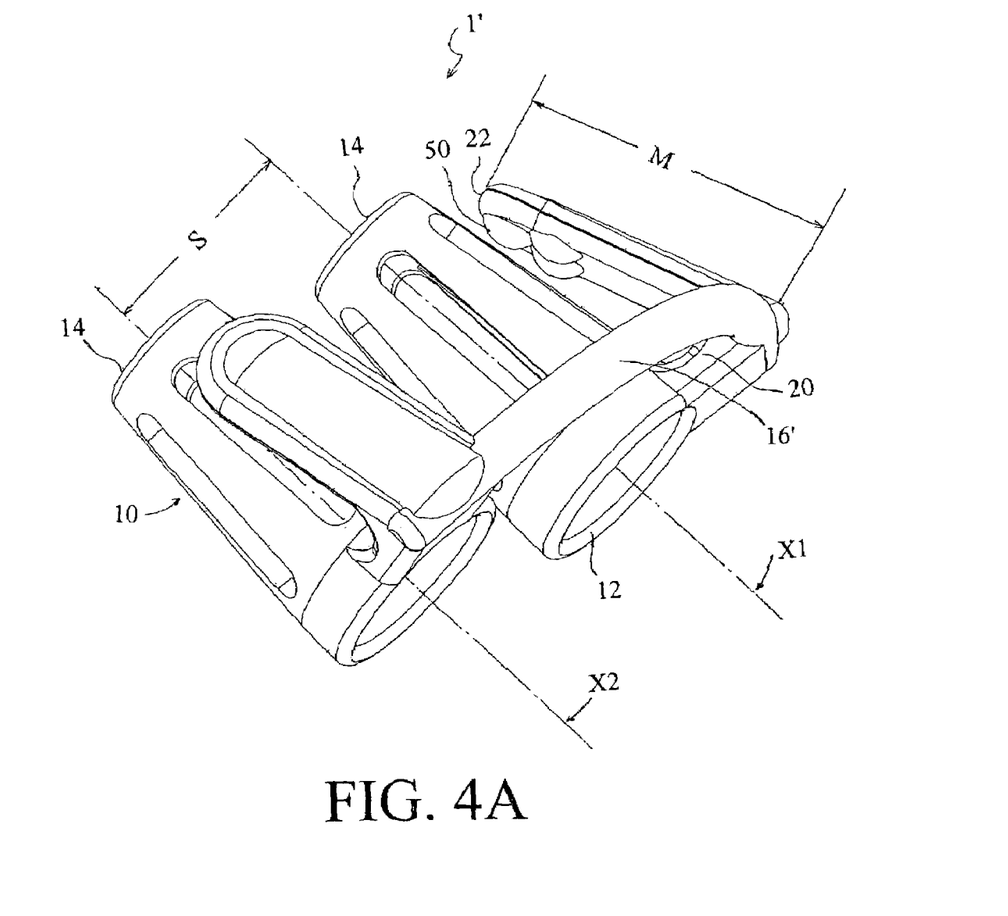
FIG. 4A is a perspective view of an alternate embodiment of the invention.

In a preferred embodiment shown in FIG. 4A, device 1' has coupler element 16' which extends between first ends 12. The central axis of coupler element 16' lies in a plane that is substantially perpendicular to the tube axes X1 and X2. In this embodiment, coupler element 16' permits relative flexing motion of device 1' so that axes X1 and X2 remain substantially parallel, but separation S of those axes varies to accommodate spacing of the nostrils.

Radially extending tab supports 20 extend from first ends 12 and connect to coupler element 16. Tabs 22 extend from tab supports 20 a distance M in the direction of the central axis to distal ends of the tabs. Tabs 22 are preferably made of nonresiliently deformable materials, for example, metal including copper, aluminum, and etc. The tab supports 20 may be made of the same or different materials as that used for the tabs 22. In use, tabs 22 remain outside the user's nostrils, and, acting as clips, help secure the device in the nostrils. The tabs 22 also function as a stop which prevent the device from being wholly inserted into a user's nostril.

Figure 4B:
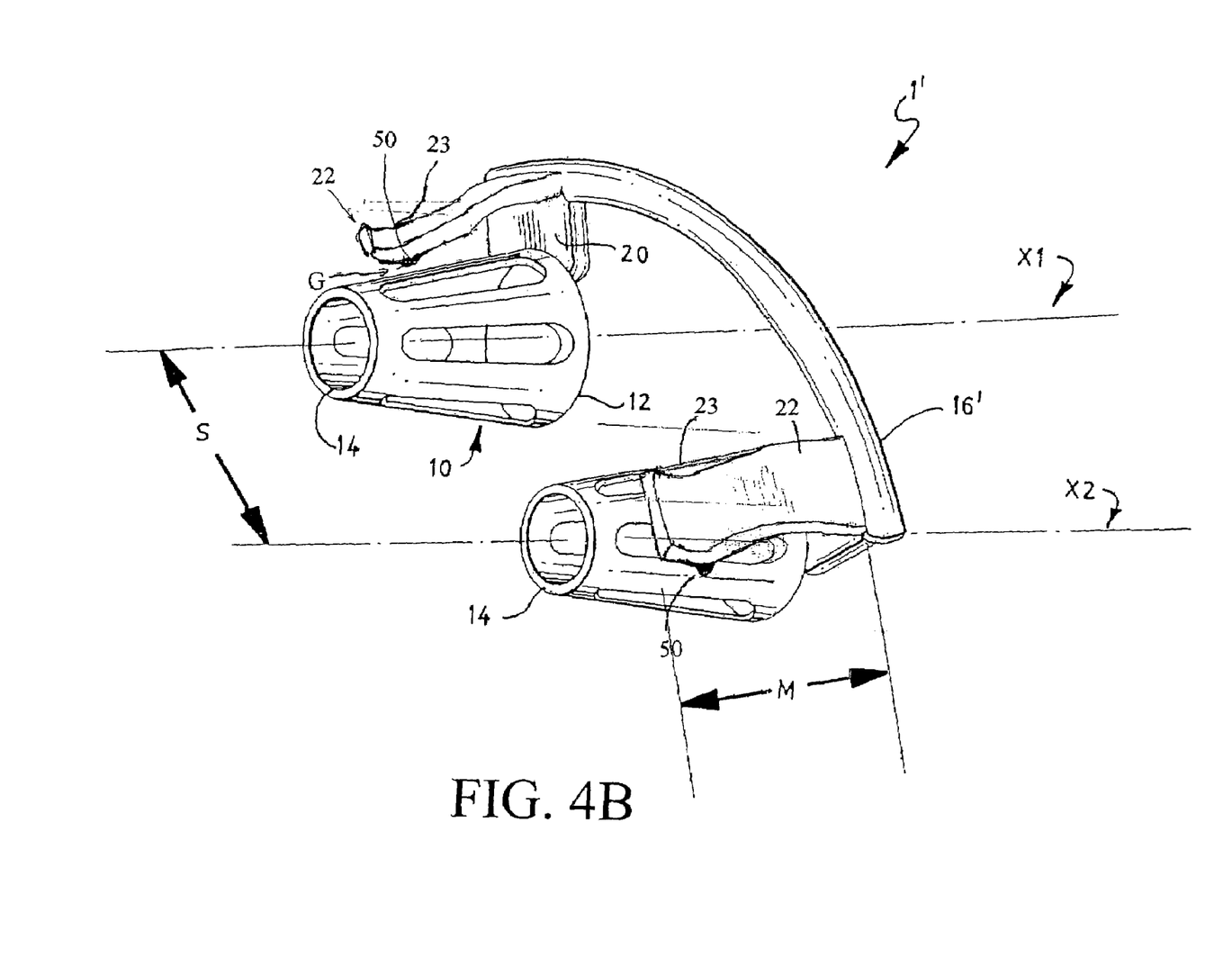
FIG. 4B is a perspective view of another alternate embodiment of the invention.

In another preferred embodiment, as shown in FIG. 4B, the tabs 22 are substantially S-shaped, and includes a distal curved portion 23 distal from the first end 12. The distal curved portion 23 defines a relatively small gap G with an outer surface of the tubular element. The tabs 22 are constructed such that the small gap G is adapted to receive a lateral wall of a user's nose, and the tabs 22 are adapted to clip on the lateral wall of the user's nose. In one preferred embodiment, the tab 22 includes at least one relatively small protrusion 50 extending from the distal curved portion 23 toward the tubular element 10, as best shown in FIG. 4B and FIG. 5B. Alternatively, the relatively small protrusion 50 may extend from the outer surface of the tubular element 10 toward the distal curved portion 23 of the tab 22. In another alternate embodiment, the tab 22 includes protrusions 50 extending from the distal curved portion 23 toward the tubular element 10, and the tubular element 10 also includes protrusions opposing to the protrusions of the tab 22. In the embodiment shown in FIG. 4A, the protrusions 50 extends from a distal end of the tab 22 toward the tubular element 10. The small protrusion helps to secure the device in the user's nostrils.

Figure 5A:
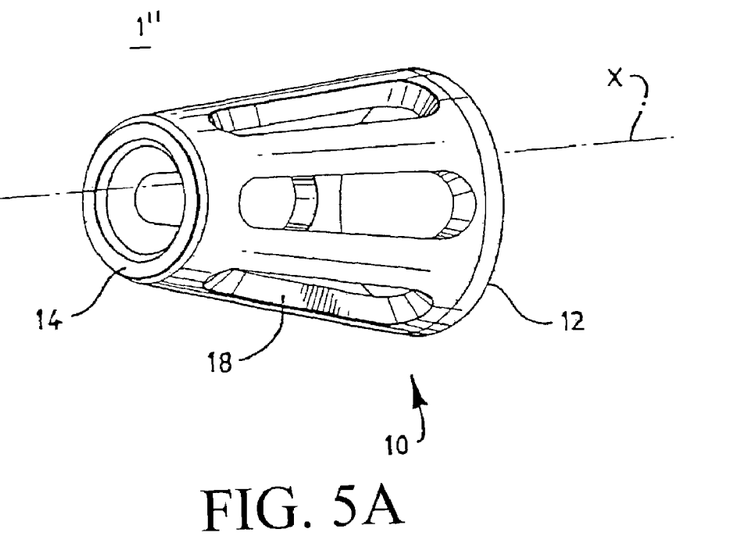
FIG. 5A is a perspective view of an alternate embodiment of the invention.
Figure 5B:
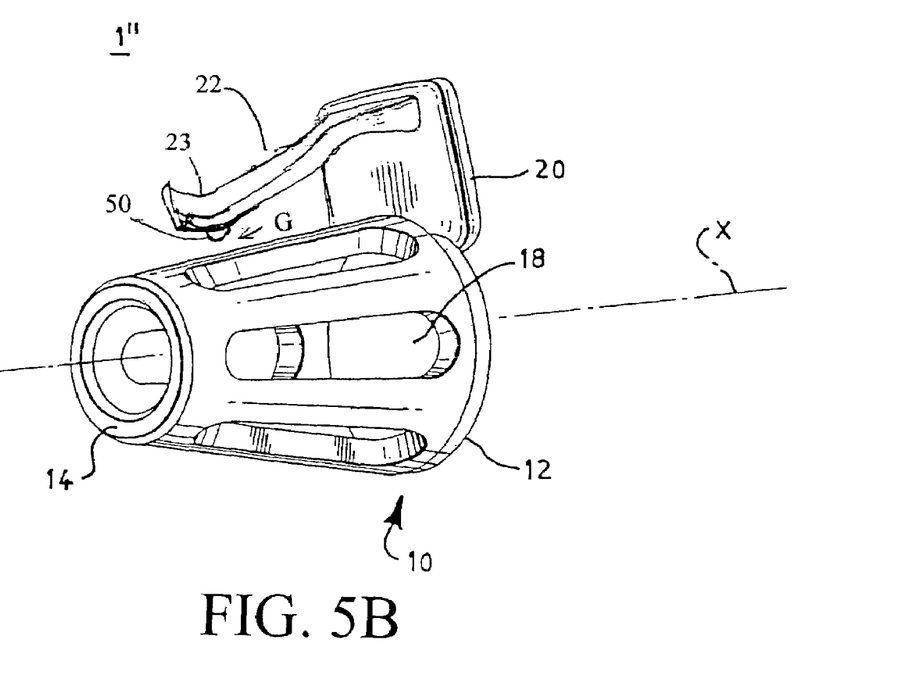
FIG. 5B is a perspective view of yet another embodiment of the invention.

FIGS. 5A-SD show other embodiments of nasal breathing assist devices. In FIG. 5A, device 1" has a tubular element 10 extending along a tube axis X between a relatively large diameter first end 12 and tapering toward a relatively smaller diameter second end 14. As previously described, tubular element 10 may have passageways 18 extending through the walls of the tubular elements transverse to tube axis X.

As shown in the embodiment in FIG. 5B, radially extending tab support 20 extends from first end 12. The substantially S-shaped non-resilient tab 22 extends from tab support 20 a distance M in the direction of axis X toward second end 14.

Figure 5C:
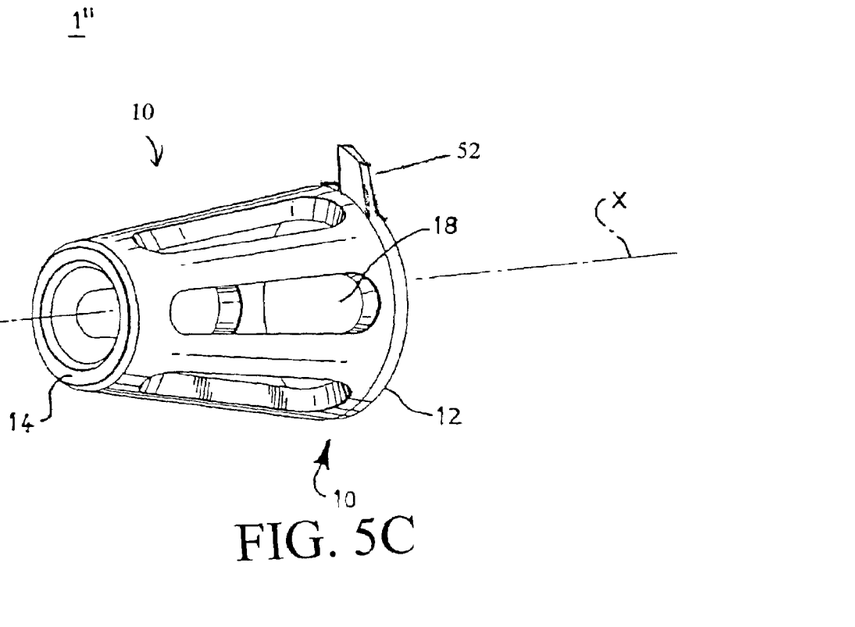
FIG. 5C is a perspective view of another embodiment of the invention.
Figure 5D:
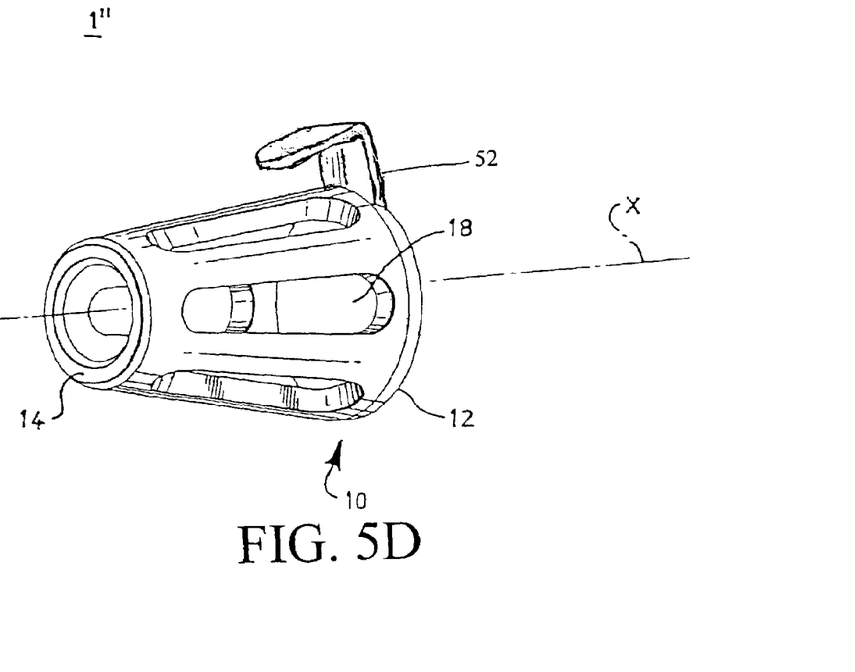
FIG. 5D is a perspective view of another embodiment of the invention.

FIG. 5C illustrates another preferred embodiment, in which the device includes a stop member 52 extending radially and outwardly from the first end 12 of the tubular element to a distal end. The stop member 52 is adapted to engage with an open end of a user's nostril to prevent the device from being wholly inserted into the nostril when the device is in use. In an alternate embodiment, as shown in FIG. 5D, the stop member may further include a protrusion extending from the distal end of the stop member toward the second 14 of the tubular element 10. In use, the protrusion remains outside the user's nostril, and, acting as a clip, helps secure the device in the nostril. Device 1" of FIGS. 5A-5D may be used singly or as a pair. The stop member 52 may also be employed in the embodiments having a pair of tubular elements connected by a coupler element.

Figure 6:
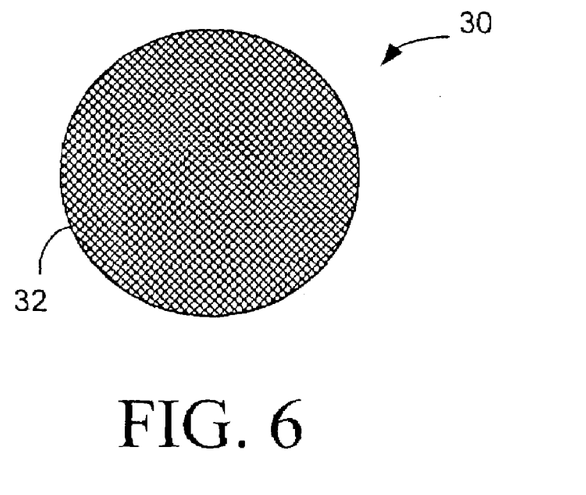
FIG. 6 shows a schematic view of a filter in accordance with one embodiment of the present invention.

FIG. 6 shows a filter 30 which may be used with the nasal breathing assist device. The filter 30 includes a filter medium, preferably a paper, a metal or plastic mesh coated with absorbent materials, spanning a frame 32. The frame 32 is preferably contoured to fit in an opened-faced inner channel 36 defined in the tubular element 10. In a preferred embodiment, the tubular element 10 includes at least one relatively small protrusion 38 extending radially from an inner surface of the inner channel 36. The frame 32 of the filter 30 is adapted to snap-fit over the protrusion 38 into the inner channel 36 and is retained by the protrusion 38, thereby the filter 30 cannot slip out of the tubular element 10 when the nasal breathing assist device is in use.

Figure 7:
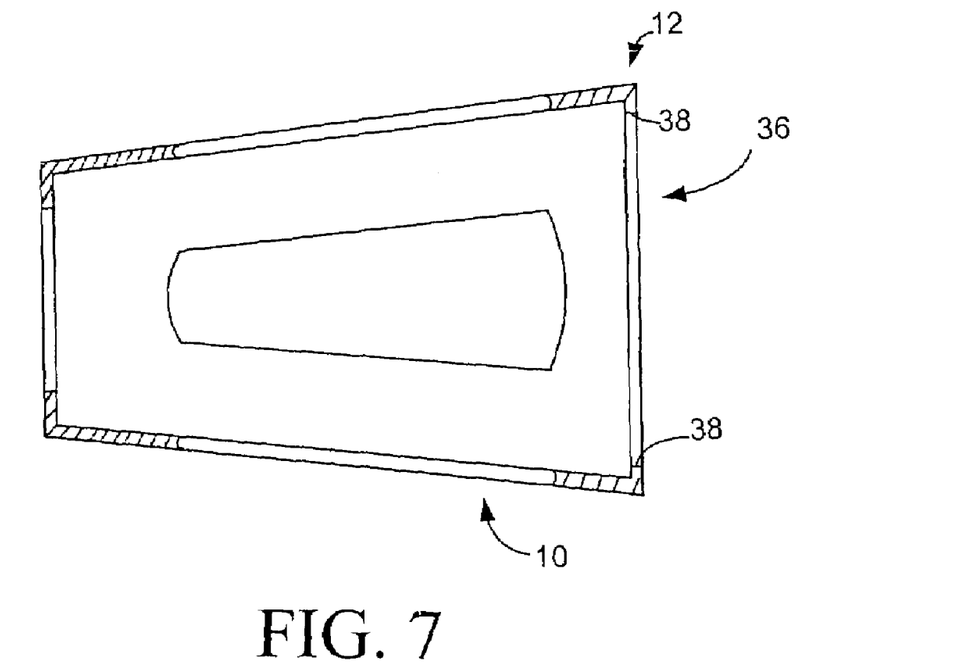
FIG. 7 shows a cross-sectional view of an alternate embodiment of the invention.
Figure 8:
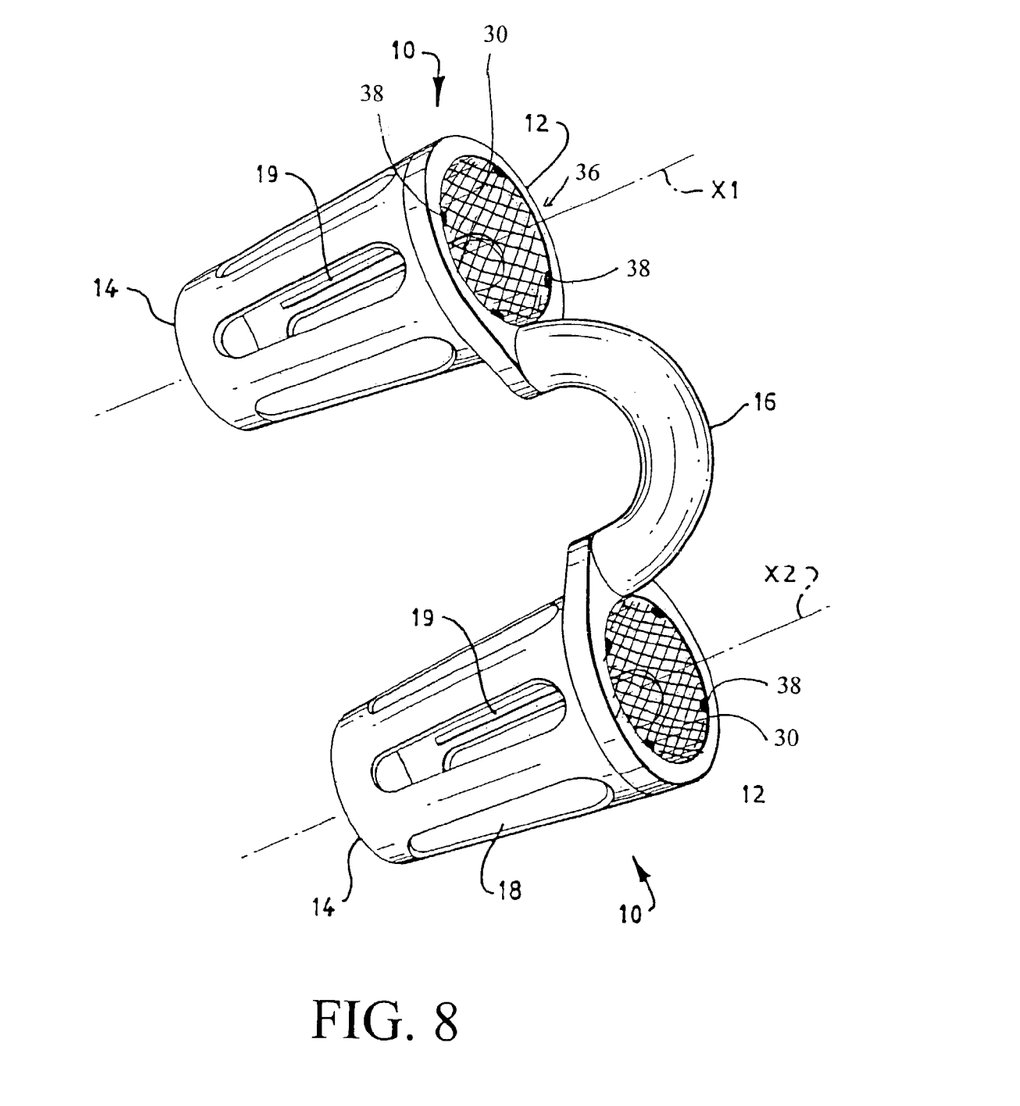
FIG. 8 shows the filter of FIG. 6 together with the nasal breathing assist device.

FIG. 7 illustrates a cross-sectional view of one tubular element 10 in accordance with one preferred embodiment of the invention. As shown in FIG. 7, the protrusion 38 extends throughout an inner circumference at the first end 12 (the end with a relatively large diameter) of the inner channel 36. The filter 30 is snap-plugged into the channel 36 from the first end of the channel 36, and because the diameter of the channel 36 tapers from the first end to the second end, the filter can be secured by the inner surface of the channel 36 and the protrusion 38. The protrusion 38 is relatively small, so that the filter 36 can by easily removed and replaced. FIG. 8 shows a schematic view of the filters 30 together with a nasal breathing assist device. Each tubular element 10 includes relatively small protrusions 38 securing the filter 30 at the first end of the tubular element 10. The filter 30 is preferably positioned at one of the two ends of the tubular element 10, so that the filter 30 can be easily removed and replaced, but the filter 30 also can be positioned at a place between the two ends and secured by protrusions extending radially adjacent that place.

Figure 9:
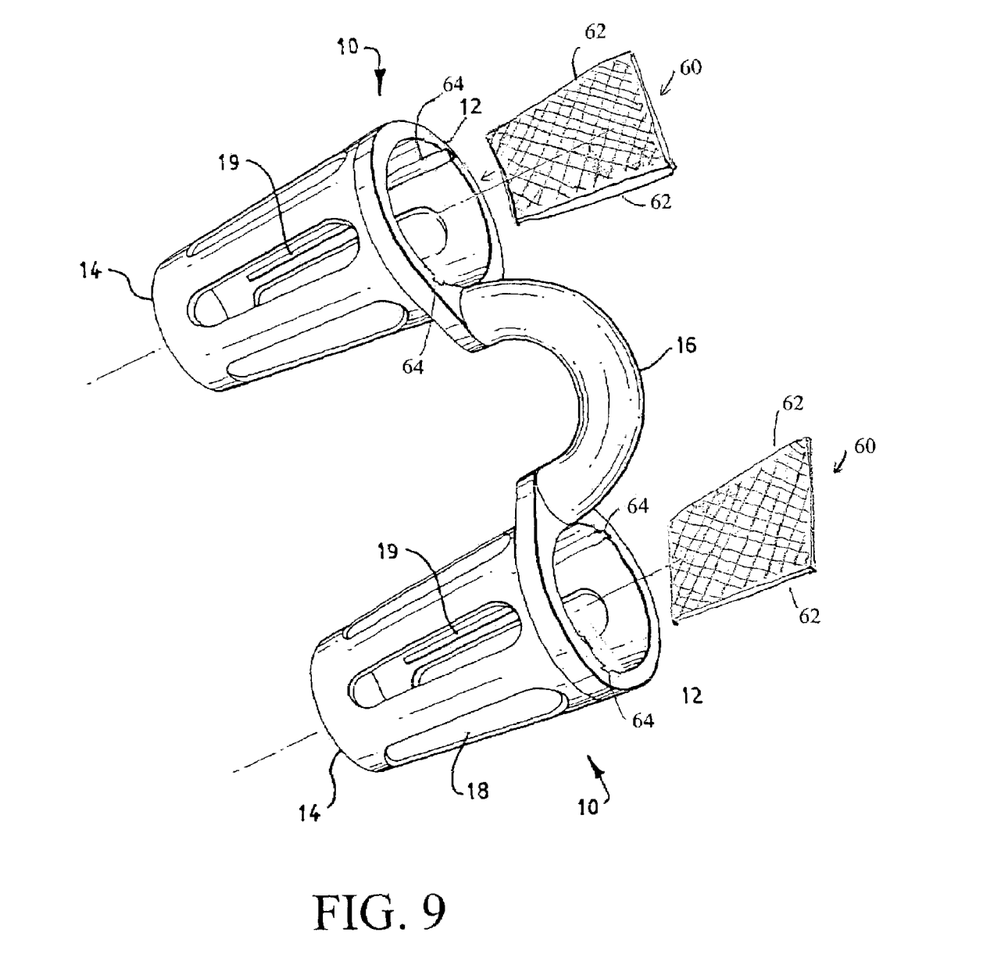
FIG. 9 shows another preferred embodiment of the invention.

FIG. 9 illustrates another preferred embodiment of the present invention. As shown in FIG. 9, The device further includes at least one removable medication carrier 60 which may include a medium adapted to bear a therapeutic agent. The removable carrier 60 preferably includes a frame tapering from a first end to a second end. The frame includes two opposite edges 62. The tubular element 10 further defines two opposing channels 64 on an inner surface of the tubular element 10. The two opposing channels 64 extend substantially in the same direction as the central axis and are adapted to receive the two opposite edges 62 of said removable carrier 60. The frame of the removable medication carrier 60 may be constructed with other shapes, and the tubular element may define corresponding channels or other mechanism for receiving the frame of the carrier 60. The therapeutic agent may be medications, for example, antibiotics, for treating chronic sinusitis or other nasal diseases.

The filter and the medication carrier are shown in use with a pair of tubular elements in the figures. However, the filter and the medication carrier can also be used with embodiments having only one tubular element as shown in FIGS. 5A-5C.

The device can be made of rigid, semi-resilient, or resilient materials. The nasal breathing assist devices can be disposable or reusable. The reusable devices can be easily cleaned by rinsing with soap and water.

Figure 10:
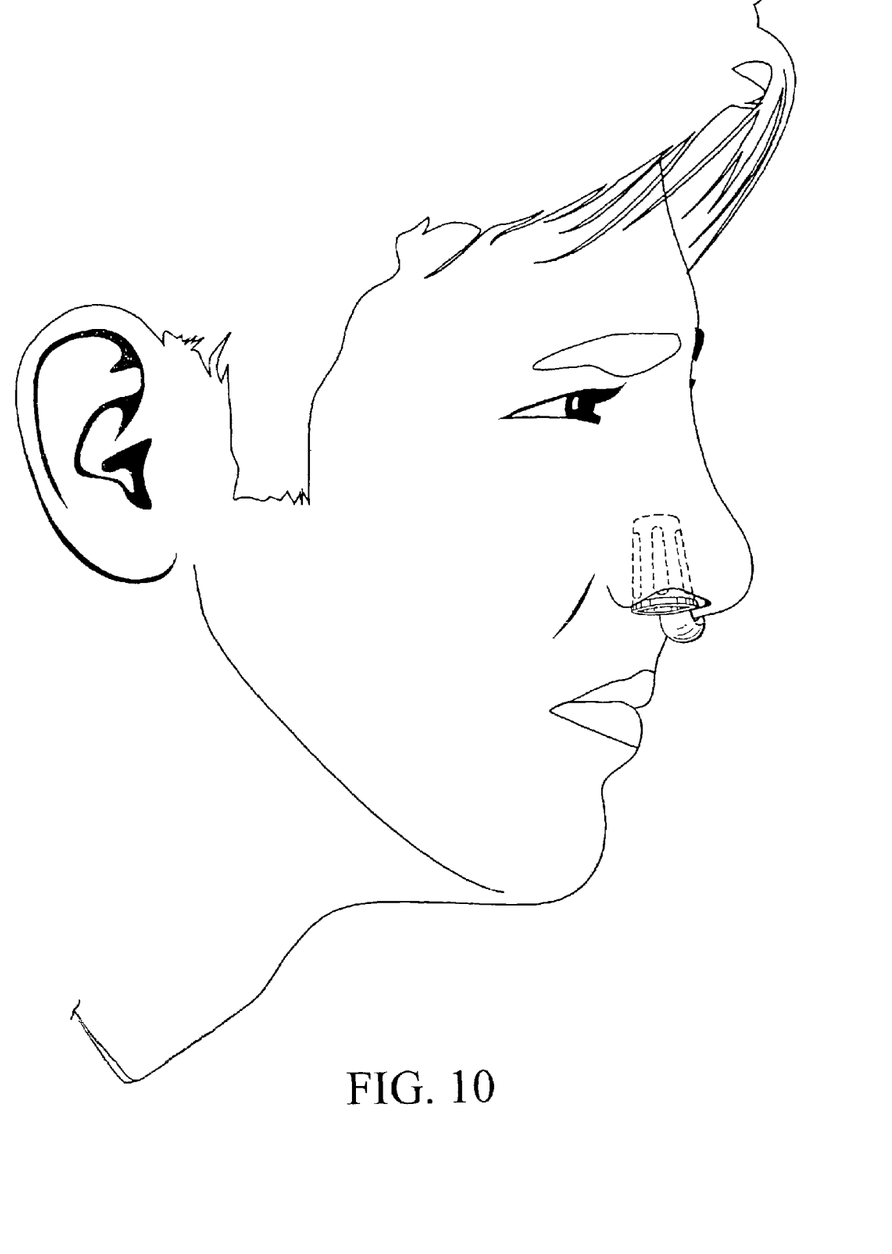
FIG. 10 is a representation of one embodiment of the invention in use.

The nasal breathing assist device is inserted in the user's nostrils, as shown in FIG. 10, usually at bedtime. The tubular elements maintain open nasal passages during sleeping, which allows the patient to obtain sufficient airflow through the nose only, rather than supplementing the air supply through the mouth. The filters can be made to absorb or hold pollen, dust, particles in smoke and smog fumes, nicotine in tobacco smoke, sulphuric acid, obnoxious odors, and other irritating elements.

The nasal breathing assist devices can be used to aid in the administration of nasally supplied drugs and medications, either at bedtime or during the day, for example, using a medication carrier inserted in the tubular element to deliver medications through the nose. The nasal breathing assist device can also be used with other conventional devices to supply drugs and medications, for example, the user can insert the device into the nose, and spray a nasal medication, or moisture mist agent into the nose. The passageways in the device act to help circulate the medication or agent within the nasal passageways by keeping the nasal passages open.

The invention may be embodied on other specific form without departing from the spirit or essential characteristics thereof. The present embodiments are therefore to be considered illustrative and not restrictive, the scope of the invention being dictated by the appended claims rather than by the foregoing description, and all changes which come within the meaning and range of equivalency of the claims are therefore intended to be embraced therein.

I claim:

1. A device for nasal insertion comprising:
   i) a pair of open-ended tubular elements, each of which extends along a respective central tube axis between a first end and a second end, said first end being larger than said second end; wherein the central tube axes of the tubular elements lie in a first plane, and wherein at least one of the tubular elements defines a groove along a lateral wall of the respective tubular element the groove being defined on a side of the lateral wall that faces the tubular element interior; and
   ii) a coupler element extending between said first ends of said tubular elements, wherein the central tube axes of the tubular elements are spaced apart at said first ends by a distance D, whereby said distance D is selected to correspond to the separation of a user's nostrils, and wherein said coupler element permits rotational motion of the central tube axes of said tubular elements.

2. The device of claim 1, wherein the groove is adapted to receive a removable carrier bearing a therapeutic agent.

3. The device of claim 1, wherein at least one of said tubular elements further comprises at least one deformable tab extending from said first end toward said second end of said tubular element to a distal end of said tab, and wherein said tab comprises a distal curved portion adjacent said distal end.

4. The device according to claim 3, wherein said tab includes at least one relatively small protrusion extending from said distal end of said tab toward said tubular element.

5. The device according to claim 3, wherein at least one of said tubular element includes at least one relatively small protrusion extending from an outer surface of said tubular element opposing said distal end of said tab.

6. The device according to claim 3, wherein said tab is substantially S-shaped.

7. The device according to claim 6, wherein said tab includes at least one relatively small protrusion extending from said distal curved portion toward said tubular element.

8. The device according to claim 6, wherein at least one of said tubular element includes at least one relatively small protrusion extending from an outer surface opposing said distal curved portion of said tab.

9. The device according to claim 3, wherein said tab is made of metal.

10. The device according to claim 9, wherein said metal is selected from the group consisting of copper and aluminum.

11. The device according to claim 1, wherein said coupler element is a resilient, nominally curved strut lying substantially in a plane substantially perpendicular to said tube axes.

12. The device according to claim 1, wherein said coupler element is a resilient, nominally curved strut lying substantially in a plane substantially parallel to said tube axes.

13. The device according to claim 1, wherein said central axes of said tubular elements are offset by an angle A and diverge from said first ends thereof.

14. The device according to claim 1, wherein the lateral wall defines at least one passageway extending therethrough transverse to said tube axis.

15. The device according to claim 14, wherein said passageway is elongated and extends at least in part in the direction of said tube axis.

16. The device according to claim 1, wherein at least one of said tubular elements includes a filter having a peripheral frame contoured to snap-fit in an open-faced channel defined in said tubular element, said filter having a filter medium spanning said frame.

17. The device according to claim 16, wherein at least one of said tubular element includes at least one relatively small protrusion extending radially from an inner surface of said channel, said peripheral frame of said filter being adapted to snap-fit in said channel and being retained by said protrusion.

18. The device according to claim 17, wherein said protrusion extends throughout an inner circumference of said channel.

19. The device according to claim 1, wherein the groove is adapted to receive medication.

20. The device according to claim 1, wherein at least one of said tubular element further defines at least one channel on an inner surface of said tubular element, said channel extending in a plane substantially parallel to said central axis, said channel being adapted to receive a removable carrier bearing a therapeutic agent.

21. The device according to claim 1, further comprising at least one removable carrier adapted to bear a therapeutic agent and adapted to be received in said tubular element, said removable carrier comprising two opposite edges, wherein at least one of said tubular element further defines two opposing channels on an inner surface of said tubular element, said two opposing channels extending in a plane substantially parallel to said central axis and being adapted to receive said two opposite edges of said removable carrier.

22. The device of claim 3, wherein said tab comprises a distal curved portion adjacent said distal end, said distal curved portion defining a relatively small gap with an outer surface of said tubular element, said gap being adaptable to receiving a lateral wall of a user's nose, and said tab being so deformable as to permit elastic deformation in use, providing a frictional holding force when engaging the nose.

23. The device of claim 1, wherein the groove does not penetrate the tubular element defining it.

24. The device of claim 1, wherein the grooved tubular element further defines at least one aperture through the lateral wall.

25. The device of claim 24, wherein the groove does not penetrate the tubular element defining it.

26. The device of claim 1, wherein the tubular elements are conic-frustum shaped.

27. A device for nasal insertion comprising an open-ended tubular element; wherein said tubular element extends along a central tube axis between a first end and a second end, said first end being larger than said second end; and wherein the tubular element defines at least one groove along a lateral wall of the tubular element, the groove being defined on a side of the lateral wall that faces the tubular element interior.

28. The device of claim 27, wherein the groove is adapted to receive a removable carrier bearing a therapeutic agent.

29. The device of claim 27, wherein said tubular element comprises at least one deformable tab extending from said first end toward said second end of said tubular element to a distal end of said tab, and wherein said tab comprises a distal curved portion adjacent said distal end.

30. The device according to claim 29, wherein said tab includes at least one relatively small protrusion extending from said distal end of said tab toward said tubular element.

31. The device according to claim 29, wherein said tubular element includes at least one relatively small protrusion extending from an outer surface of said tubular element opposing said distal end of said tab.

32. The device according to claim 29, wherein said tab is substantially S-shaped.

33. The device according to claim 32, wherein said tab includes at least one relatively small protrusion extending from said distal curved portion toward said tubular element.

34. The device according to claim 32, wherein said tubular element includes at least one relatively small protrusion extending from an outer surface opposing said distal curved portion of said tab.

35. The device according to claim 29, wherein said tab is made of metal.

36. The device according to claim 29, wherein said metal is selected from the group consisting of copper and aluminum.

37. The device of claim 29, wherein said distal curved portion defines a relatively small gap with an outer surface of said tubular element, said gap being adaptable to receiving a lateral wall of a user's nose, and said tab being so deformable as to permit elastic deformation in use, providing a frictional holding force when engaging the nose.

38. The device according to claim 27, wherein the lateral wall defines at least one passageway extending therethrough transverse to said tube axis.

39. The device according to claim 38, wherein said passageway is elongated and extends at least in part in the direction of said tube axis.

40. The device according to claim 27, wherein said tubular element comprises a filter having a peripheral frame adapted to be snap-fitted in an open-faced channel defined in said tubular element.

41. The device according to claim 40, wherein said filter having a filter medium spanning said frame.

42. The device according to claim 40, wherein said tubular element includes at least one relatively small protrusion extending radially from an inner surface of said channel, said peripheral frame of said filter being adapted to snap-fit in said channel and being retained by said protrusion.

43. The device according to claim 42, wherein said protrusion extends throughout an inner circumference of said channel.

44. The device according to claim 27, wherein said groove is adapted to receive medication.

45. The device according to claim 27, wherein said tubular element further defines at least one channel on an inner surface of said tubular element, said channel extending substantially parallel to said central axis, said channel being adapted to receive a removable medication carrier adapted for bearing a therapeutic agent.

46. The device according to claim 27, further comprising at least one medication carrier adapted to bear a therapeutic agent and adapted to be received in said tubular element, said removable carrier comprising two opposite edges, wherein said tubular element further defines two opposing channels on an inner surface of said tubular element, said two opposing channels extending in a plane substantially parallel to said central axis and being adapted to receive said two opposite edges of said removable carrier.

* * * * *